(12) United States Patent
Prindiville

(10) Patent No.: US 10,354,374 B1
(45) Date of Patent: Jul. 16, 2019

(54) METHOD OF REPRESENTING THE INTERNAL CONDITIONS IN COMPUTED TOMOGRAPHY

(71) Applicant: James Edward Prindiville, Lincoln, CA (US)

(72) Inventor: James Edward Prindiville, Lincoln, CA (US)

( * ) Notice: Subject to any disclaimer, the term of this patent is extended or adjusted under 35 U.S.C. 154(b) by 0 days.

(21) Appl. No.: 16/287,954

(22) Filed: Feb. 27, 2019

Related U.S. Application Data (60) Provisional application No. 62/635,829, filed on Feb. 27, 2018.

(51) Int. Cl.
*G06K 9/00* (2006.01)
*G06T 7/00* (2017.01)
(Continued)

(52) U.S. Cl.
CPC ............ *G06T 7/0004* (2013.01); *A61B 6/032* (2013.01); *A61B 6/035* (2013.01); *A61B 6/58* (2013.01);
(Continued)

(58) Field of Classification Search
CPC ... G06T 7/0004; G06T 7/0012; G06T 11/003; G06T 11/005; G06T 11/006; G06T 11/008; G06T 2207/10072; G06T 2207/10081; G06T 2207/10116; G06T 2207/30004; A61B 6/03; A61B 6/032; A61B 6/035; A61B 6/0457; A61B 6/5258; A61B 6/547; A61B 6/58; A61B 6/581; A61B 6/582; A61B 6/583; A61B 6/584; A61B 6/585; A61B 6/586; A61B 6/587; A61B 6/588; A61B 6/589; A61B 8/58; A61B 8/582; A61B 8/587; G01N 23/02; G01N 23/04; G01N 23/046; G01N 23/083; G01N 23/085; G01N 23/087; G01N 23/223; G01N 2223/03; G01N 2223/04; G01N 2223/303; G01N 2223/3035; G01N 2223/309; G01N 2223/33; G01N 2223/3306;
(Continued)

(56) References Cited

U.S. PATENT DOCUMENTS 6,047,041 A * 4/2000 Ellinger .................. G01N 23/04
378/57
7,775,715 B2 * 8/2010 Warner ................ G01N 23/046
378/20

(Continued)

*Primary Examiner* — Eric Rush (57) ABSTRACT

A method for validating computed tomography (CT) techniques and individual inspections is provided with a CT reconstruction algorithm, an x-ray source, a primary rotational stage, a secondary rotational stage, and an x-ray beam detector. A test object is situated on the primary rotational stage and a plurality of image quality indicators (IQIs) is situated on the secondary rotational stage. The x-ray source, the primary rotational stage, the secondary rotational stage, and the x-ray beam detector are linearly aligned. Therefore, an x-ray beam from the x-ray source intersects the test object and the IQIs before reaching the x-ray beam detector. A CT reconstruction is developed by superimposing a plurality of projection data from the test object and the IQIs. More specifically, a CT reconstruction from the IQIs with a specific intensity value is added to the CT reconstruction of the test object.

12 Claims, 9 Drawing Sheets

(51) Int. Cl.
*G06T 11/00* (2006.01)
*G01N 23/046* (2018.01)
*A61B 6/03* (2006.01)
*A61B 6/00* (2006.01)
*A61N 5/10* (2006.01)

(52) U.S. Cl.
CPC .............. *A61B 6/582* (2013.01); *A61B 6/583* (2013.01); *A61N 5/1075* (2013.01); *G01N 23/046* (2013.01); *G06T 11/005* (2013.01); *G06T 11/006* (2013.01); *A61N 2005/1076* (2013.01); *G01N 2223/303* (2013.01); *G01N 2223/3306* (2013.01); *G01N 2223/401* (2013.01); *G01N 2223/419* (2013.01); *G01N 2223/645* (2013.01); *G06T 2207/10081* (2013.01); *G06T 2207/10116* (2013.01)

(58) Field of Classification Search
CPC ......... G01N 2223/40; G01N 2223/401; G01N 2223/419; G01N 2223/645; A61N 5/1075; A61N 2005/1076
USPC ....... 382/100, 128, 131, 132, 141, 154, 254, 382/274–276, 312; 378/1, 4, 8, 15, 378/18–21, 62, 68, 69, 204, 205, 207, 378/208, 210, 901; 250/252.1, 336.1, 250/358.1, 360.1, 363.07, 363.09, 370.08, 250/370.09, 371, 393, 395, 491.1, 492.1, 250/505.1, 506.1, 518.1; 356/213, 215, 356/229, 234, 235, 236, 248; 324/308
See application file for complete search history.

(56) References Cited

U.S. PATENT DOCUMENTS

| | | | |
|---|---|---|---|
| 8,764,290 B2 * | 7/2014 | O'Hare | G01T 7/005 378/18 |
| 8,777,485 B2 * | 7/2014 | Holt | A61B 6/583 378/18 |
| 9,625,257 B2 * | 4/2017 | Christoph | A61B 6/583 |
| 9,826,953 B2 * | 11/2017 | Siewerdsen | A61B 6/032 |
| 10,154,821 B2 * | 12/2018 | Kawata | A61B 6/585 |
| 2017/0109904 A1 * | 4/2017 | Huang | G06T 11/008 |
| 2019/0001156 A1 * | 1/2019 | Tulik | A61N 5/1075 |

* cited by examiner

METHOD OF REPRESENTING THE INTERNAL CONDITIONS IN COMPUTED TOMOGRAPHY

The current application claims a priority to the U.S. Provisional Patent application Ser. No. 62/635,829 filed on Feb. 27, 2018.

FIELD OF THE INVENTION

The present invention relates generally to the evaluation of Computed Tomography (CT) techniques and inspections. More specifically, the present invention introduces a method for validating a CT technique and individual inspections by utilizing an external manipulator and a set image quality indicators (IQIs).

BACKGROUND OF THE INVENTION

Traditional industrial radiographic inspections have for many years utilized Image Quality Indicators (IQIs), which can be hole and/or wire type, to validate radiographic techniques and inspections. Radiographic film techniques and inspections have required that plaques of given materials and thicknesses with specified hole diameters and/or wires with specified diameters to be appropriately placed on the part to be inspected and that the required plaque hole and/or wire be clearly visible in the resulting radiograph. The proper application of these IQIs has been commonly accepted as validation for a given radiographic film technique and inspection.

Newer digital radiographic inspection techniques (i.e. digital and computed radiography and computed tomography) present several issues with respect to the application of these traditional plaque and wire type IQIs. In the case of digital radiography (DR) and computed radiography (CR), their characteristic responses for spatial resolution and contrast to noise ratio (CNR) are significantly different than film. Traditional IQIs may not be sufficient to validate a DR or CR technique or inspection. Representative Quality Indications (RQIs) are used when traditional IQIs are not adequate. For computed tomography (CT), the three-dimensional scanning and imaging capability tend to invalidate any IQI placed on the exterior of a part. For CT technique validation, RQIs are commonly required (ASTM E1570 Standard Practice for Computed Tomographic (CT) Examination).

RQIs are defined in ASTM E1817, Standard Practice for Controlling Quality of Radiological Examination by Using Representative Quality Indicators (RQIs). The RQI is an object that is representative of the part being inspected. It also contains known indications that are representative of the inspection criteria/defective conditions. It can be a fabricated or an actual production part. In either case, the RQI shall be characterized and the dimensional measurements of anomalous indicators confirmed. It is common to refer to RQIs used for CT as Phantoms.

For many of the industrial CT applications, the cost to design, build, and characterize an appropriate RQI can be extremely high. In programs with limited production runs and/or very costly items, this cost cannot be supported. In some cases, it may not even be possible to build and characterize the RQI no matter what the cost. As a result, CT inspections are being performed without validating either the capability of the inspection technique or sensitivity of a given inspection.

The objective of the present invention is to address the aforementioned issue. In particular, the present invention introduces a CT technique that utilizes an additional manipulator with the IQIs. By utilizing the present invention, internal conditions of a test object can be simulated.

DETAIL DESCRIPTIONS OF THE INVENTION

All illustrations of the drawings are for the purpose of describing selected versions of the present invention and are not intended to limit the scope of the present invention.

The present invention introduces a method for validating computed tomography techniques and individual inspections. Even with the use of various phantoms and various image quality indicators (IQIs), the internal conditions of a test object cannot be examined. However, by utilizing the method introduced by the present invention, the use of expensive phantoms can be eliminated, and the internal conditions of a test object can be successfully examined. Moreover, the present invention can be used to evaluate the sensitivity of computed tomography (CT) techniques and inspections.

Figure 1:
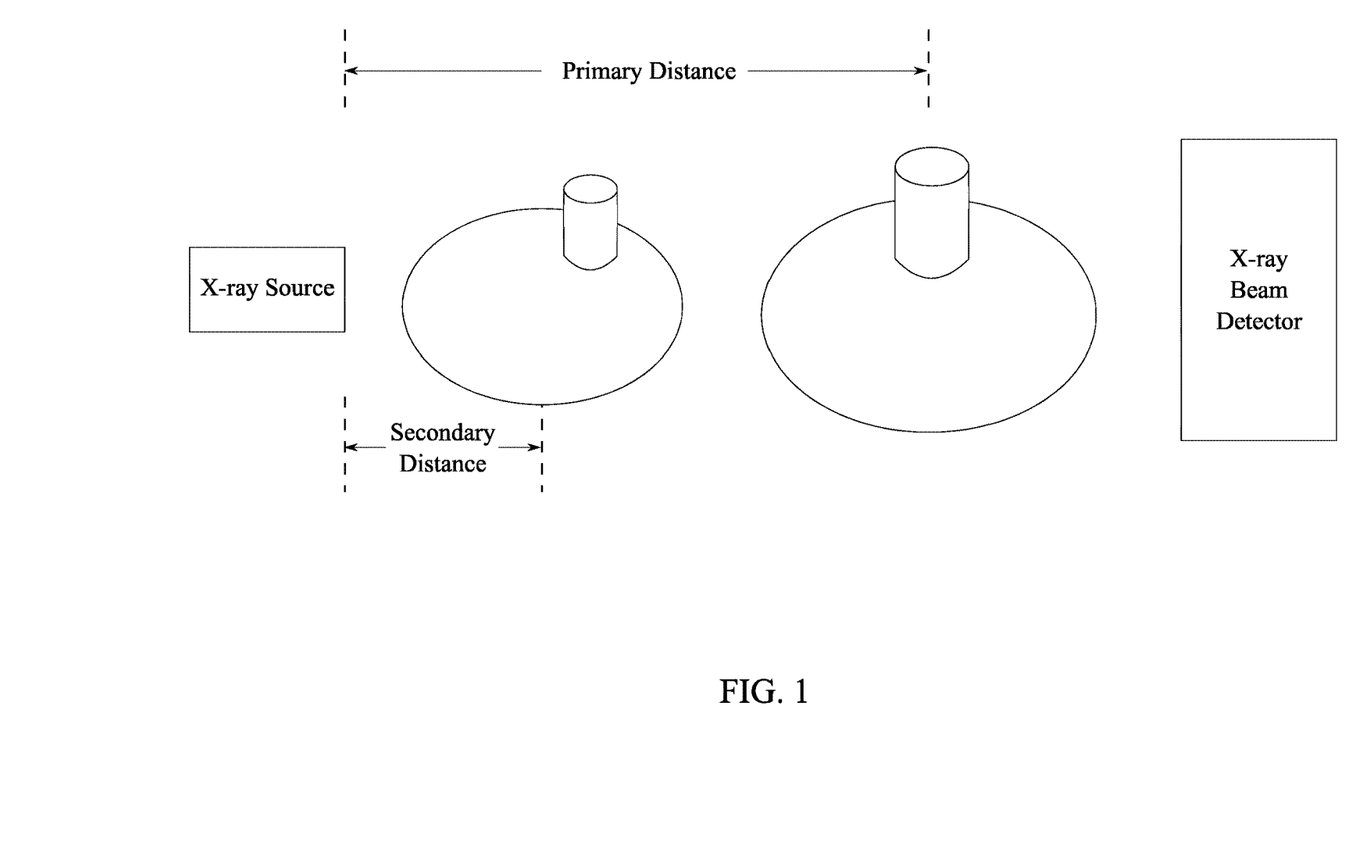
FIG. 1 is an illustration of the x-ray source, the primary rotational stage, the secondary rotational stage, and the x-ray beam detector, wherein the secondary rotational stage is positioned between the x-ray source and the primary rotational stage.
Figure 2:
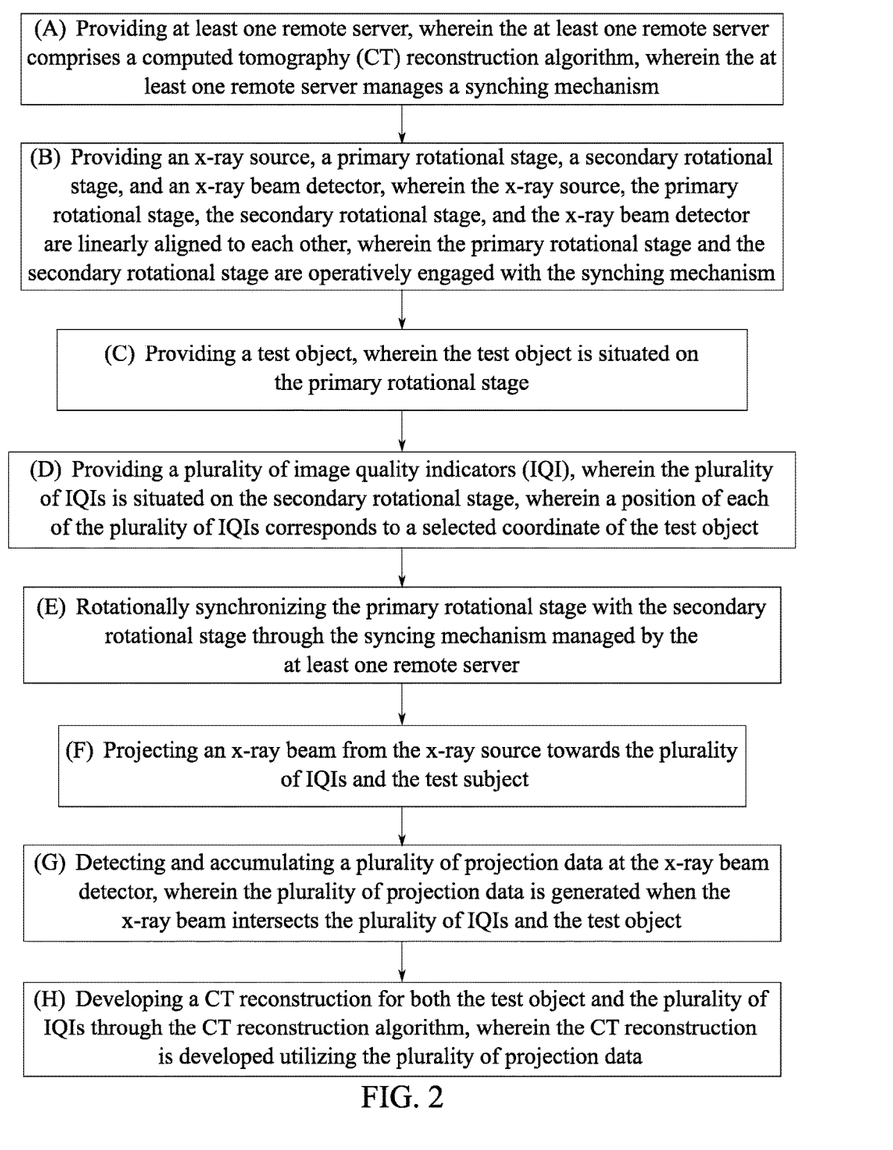
FIG. 2 is a flowchart illustrating the basic overall process of the present invention.

In order to fulfill the intended functionalities, the present invention is provided with at least one remote server that comprises a computed tomography (CT) reconstruction algorithm that is used to derive information related to a test object, wherein the test object is provided. As illustrated in FIG. 2, to execute the CT process, the present invention is provided with an x-ray source, a primary rotational stage, a secondary rotational stage, and an x-ray beam detector. As shown in FIG. 1, the x-ray source, the primary rotational stage, the secondary rotational stage, and the x-ray beam detector are linearly aligned to each other such that the primary rotational stage and the secondary rotational stage are positioned in between the x-ray source and the x-ray beam detector. The linear alignment ensures that an x-ray beam emitted from the x-ray source passes the secondary rotational stage and the primary rotational stage before reaching the x-ray beam detector for CT reconstruction purposes. The x-ray beam detector can vary in different embodiments of the present invention. Preferably, a two-dimensional digital flat panel or a linear diode array is used as the x-ray beam detector.

Figure 8:
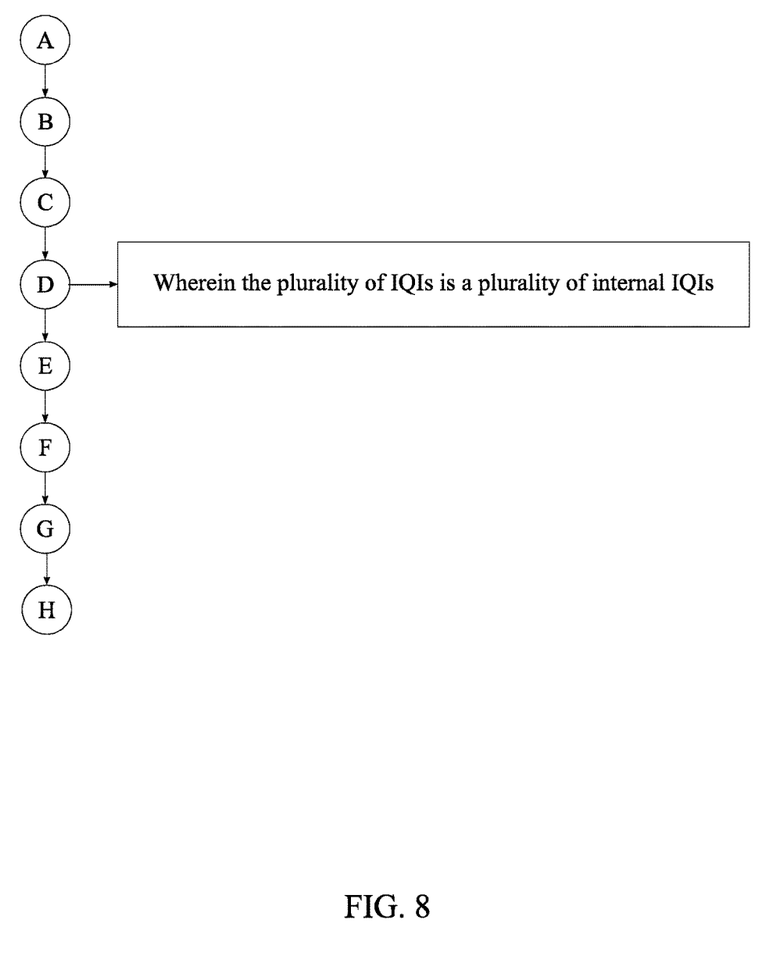
FIG. 8 is a flowchart illustrating the basic overall process of the present invention, wherein the plurality of IQIs is plurality of internal IQIs.
Figure 9:
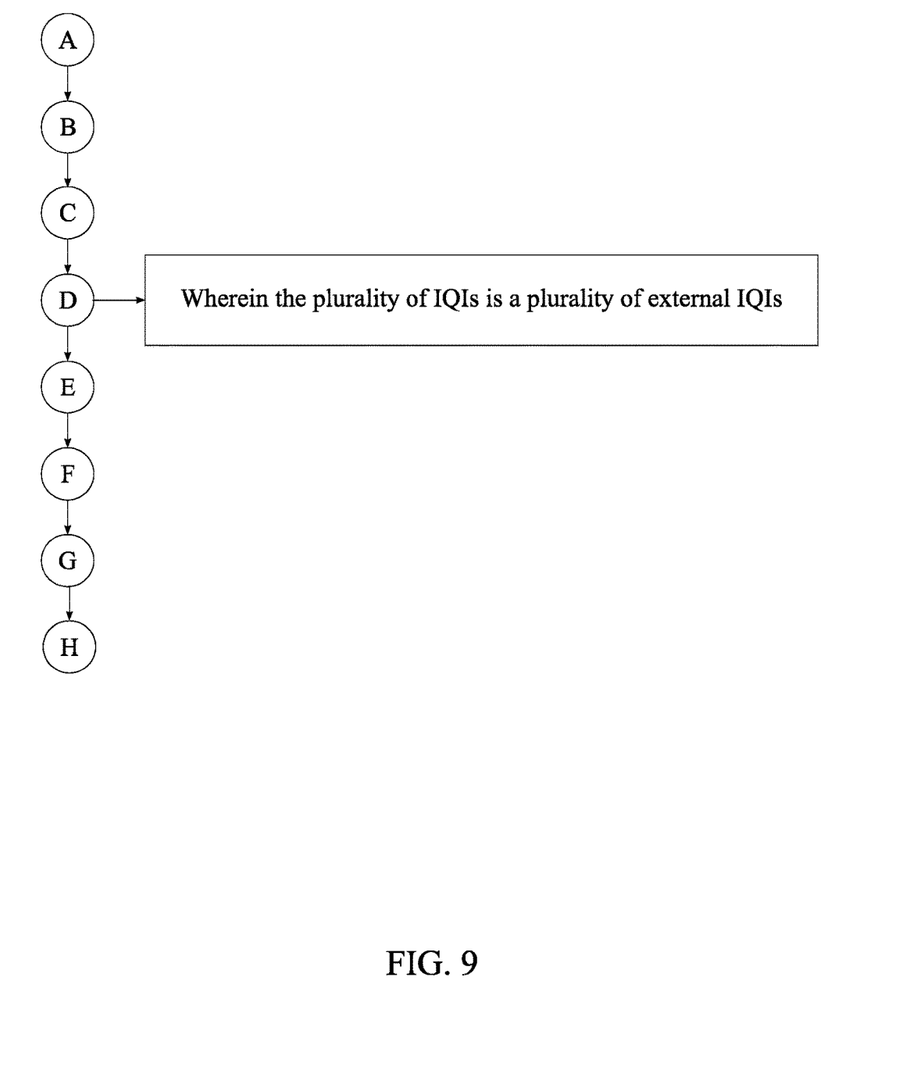
FIG. 9 is a flowchart illustrating the basic overall process of the present invention, wherein the plurality of IQIs is a plurality of external IQIs.

The test object, which is examined through the CT process, is situated on the primary rotational stage. The test object can vary in different embodiments of the present invention. In order to examine the internal conditions of the test object, the present invention is provided with a plurality of IQIs which is situated on the secondary rotational stage. The plurality of IQIs is situated on the secondary rotational stage such that a position of each of the plurality of IQIs corresponds to a selected coordinate of the test object. As shown in FIG. 8, based upon the need and the characteristics of the test object, the plurality of IQIs can be a plurality of internal IQIs in one embodiment of the present invention. As shown in FIG. 9, in another embodiment of the present invention, the plurality of IQIs can be a plurality of external IQIs. Thus, the position of each of the plurality of IQIs and the selected coordinate of the test object can vary from one embodiment to another. The total number of IQIs and the type of each of the plurality of IQIs can vary in different embodiments of the present invention. As an example, if 12 IQIs were situated on the secondary rotational stage, the 12 IQIs can consist of, but is not limited to, light-metal wires, light-metal hollow rods, and light-metal plugs.

Figure 3:
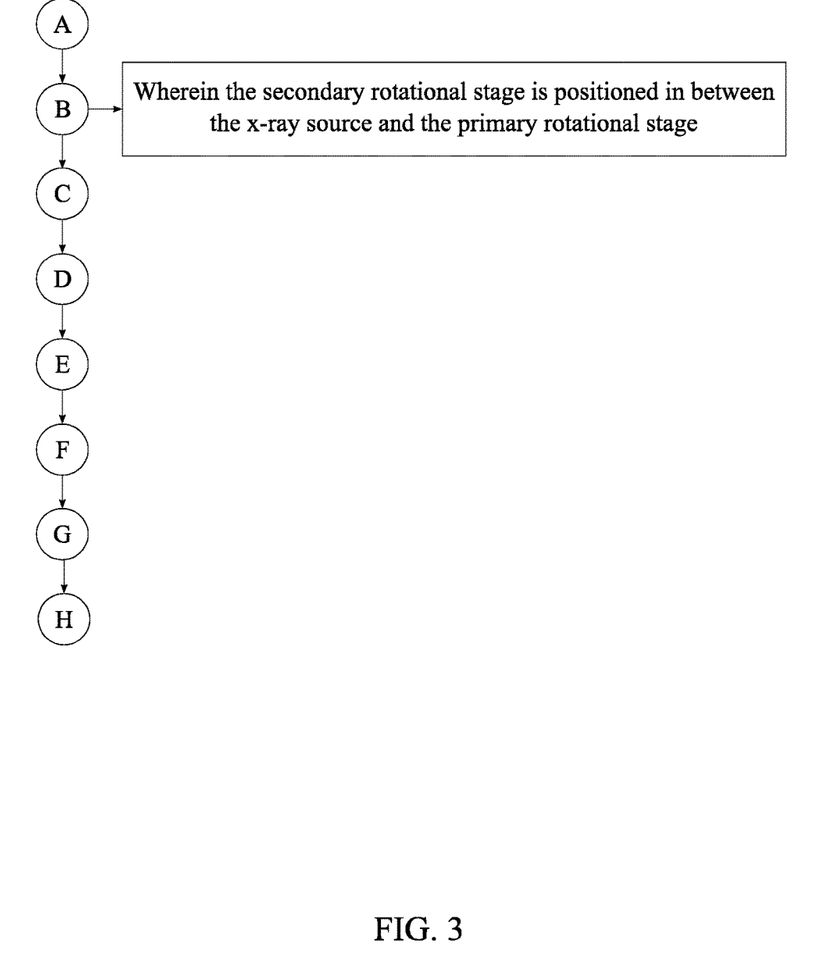
FIG. 3 is a flowchart illustrating the basic overall process of the present invention, wherein the secondary rotational stage is positioned in between the x-ray source and the primary rotational stage.
Figure 4:
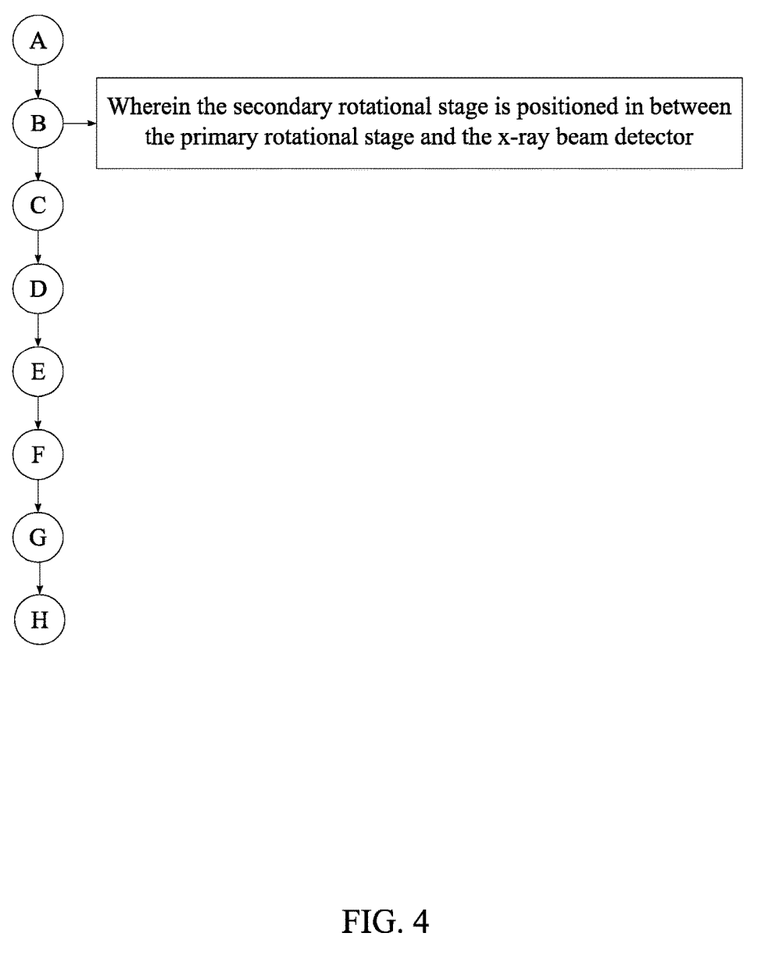
FIG. 4 is a flowchart illustrating the basic overall process of the present invention, wherein the secondary rotational stage is positioned in between the primary rotational stage and the x-ray beam detector.

As shown in FIG. 1 and FIG. 3, in one embodiment of the present invention, the secondary rotational stage can be positioned in between the x-ray source and the primary rotational stage. Thus, when the x-ray beam is emitted from the x-ray source, the x-ray beam initially passes the plurality of IQIs and then passes the test object. As shown in FIG. 4, in another embodiment of the present invention, the secondary rotational stage can be positioned in between the primary rotational stage and the x-ray beam detector. Thus, when the x-ray beam is emitted from the x-ray source, the x-ray beam initially passes the test object and then passes the plurality of IQIs. Regardless of the order in which the primary rotational stage and the secondary rotational stage are positioned, the x-ray beam passes through both the test object and the plurality of IQIs. Thus, when the CT process is executed, a resulting CT reconstruction would be representative of both the test object and the plurality of IQIs.

To execute the CT process while maintaining the proper orientation between the plurality of IQIs and the test object, the primary rotational stage is rotationally synchronized with the secondary rotational stage through a synching mechanism that is managed by the at least one remote server. However, in another embodiment of the present invention, the primary rotational stage can be rotationally synchronized with the secondary rotational stage mechanically. The primary rotational stage and the secondary rotational stage are operatively engaged with the synching mechanism so that the angular rotation of the secondary rotational stage can be matched to the angular rotation of the primary rotational stage. When the x-ray source, the primary rotational stage, the secondary rotational stage, and the x-ray beam detector are linearly aligned as previously discussed, the x-ray source projects an x-ray beam towards the plurality of IQIs and the test subject. When the x-ray beam intersects the plurality of IQIs and the test object, a plurality of projection data is generated. For CT reconstruction purposes, the x-ray beam detector proceeds to detect and accumulate the plurality of projection data. When the plurality of projection data is received at the x-ray beam detector, the present invention proceeds to develop a CT reconstruction for both the test object and the plurality of IQIs by utilizing the plurality of projection data as an input in the CT reconstruction algorithm. A size ratio between the CT reconstruction for the test object and the CT reconstruction for the plurality of IQIs is designed to be 1:1. Thus, when the CT reconstruction process is complete, the plurality of IQIs appears to be positioned at the same distance from the x-ray source as the test object.

Figure 5:
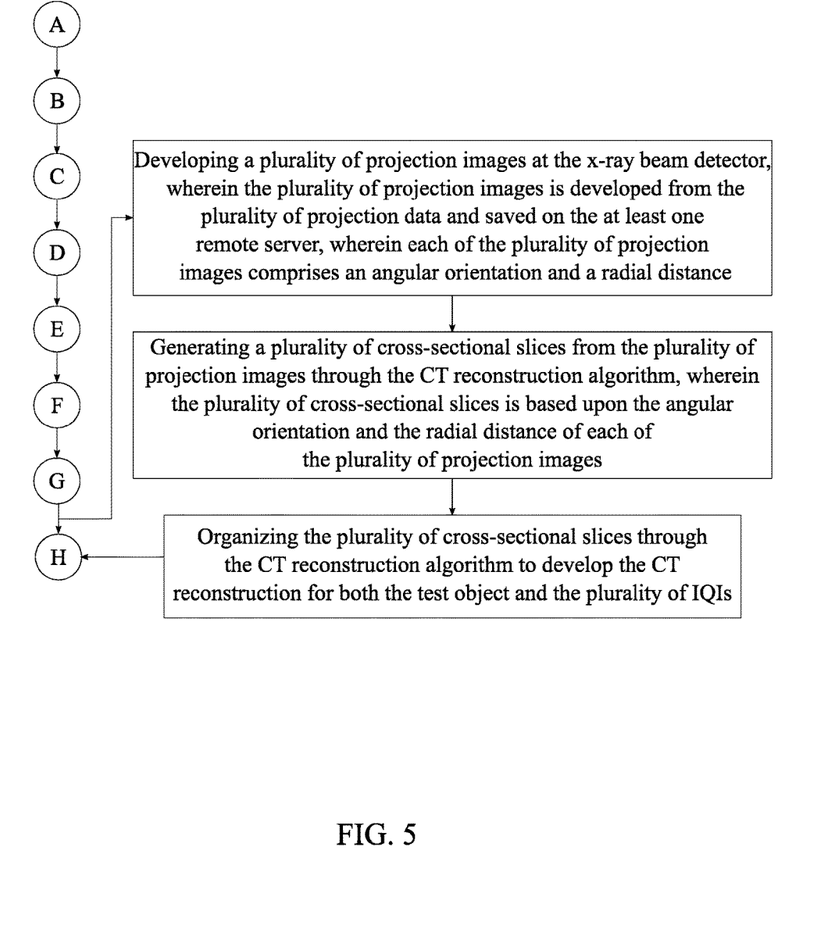
FIG. 5 is a flowchart illustrating the basic overall process of utilizing the plurality of projection data for developing a CT reconstruction.

As shown in FIG. 5, in the process of developing the CT reconstruction for both the test object and the plurality of IQIs, the present invention initially develops a plurality of projection images at the x-ray beam detector by utilizing the plurality of projection data. Each of the plurality of projection images, which are saved on the at least one remote server, comprises an angular orientation and a radial distance. Additionally, each of the plurality of projection images also comprises a corresponding intensity value. The CT reconstruction algorithm utilizes the radial distance and the angular orientation of each of the plurality of projection images along with the corresponding intensity value of each of the plurality of projection images to generate a plurality of cross-sectional slices. The plurality of cross-sectional slices is organized through the CT reconstruction algorithm to develop the CT reconstruction for both the test object and the plurality of IQIs, wherein the CT reconstruction is a 3-dimensional representation of both the test object and the plurality of IQIs.

Figure 6:
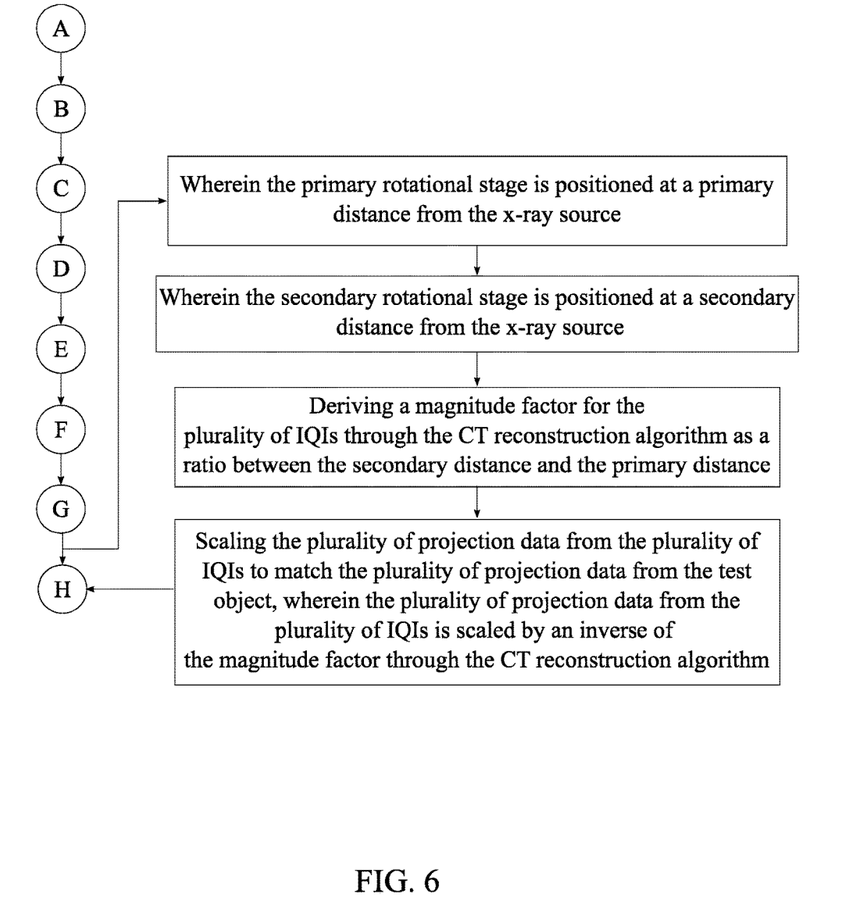
FIG. 6 is a flowchart illustrating the basic overall process of calculating the magnitude factor.

As discussed earlier, the x-ray source, the primary rotational stage, the secondary rotational stage, and the x-ray beam detector are linearly aligned to each other. As shown in FIG. 6, a distance from the x-ray source to the secondary rotational stage and a distance from the x-ray source to the primary rotational stage are used to determine a magnitude factor that is used for scaling the physical size of the plurality of IQIs for the CT reconstruction for the plurality of IQIs, wherein the magnitude factor is derived through the CT reconstruction algorithm. If the primary rotational stage is positioned at a primary distance from the x-ray source, and the secondary rotational stage is positioned at a secondary distance from the x-ray source, the magnitude factor is derived as a ratio between the secondary distance and the primary distance. The magnitude factor ensures that a size ratio between the CT reconstruction for the test object and the CT reconstruction for the plurality of IQIs is 1:1. To do so, the plurality of projection data from the plurality of IQIs is scaled to match a size of the CT reconstruction developed for the test object. In doing so, the CT reconstruction algorithm scales the size of the plurality of IQIs by an inverse of the magnitude factor. As an example, we will consider the secondary distance to be 24-inches and the primary distance to be 30-inches. As a result, the magnitude factor will be 24:30. To obtain the CT reconstruction for a 0.5-inch diameter rod, an IQI with a 0.4-inch diameter will be used.

Figure 7:
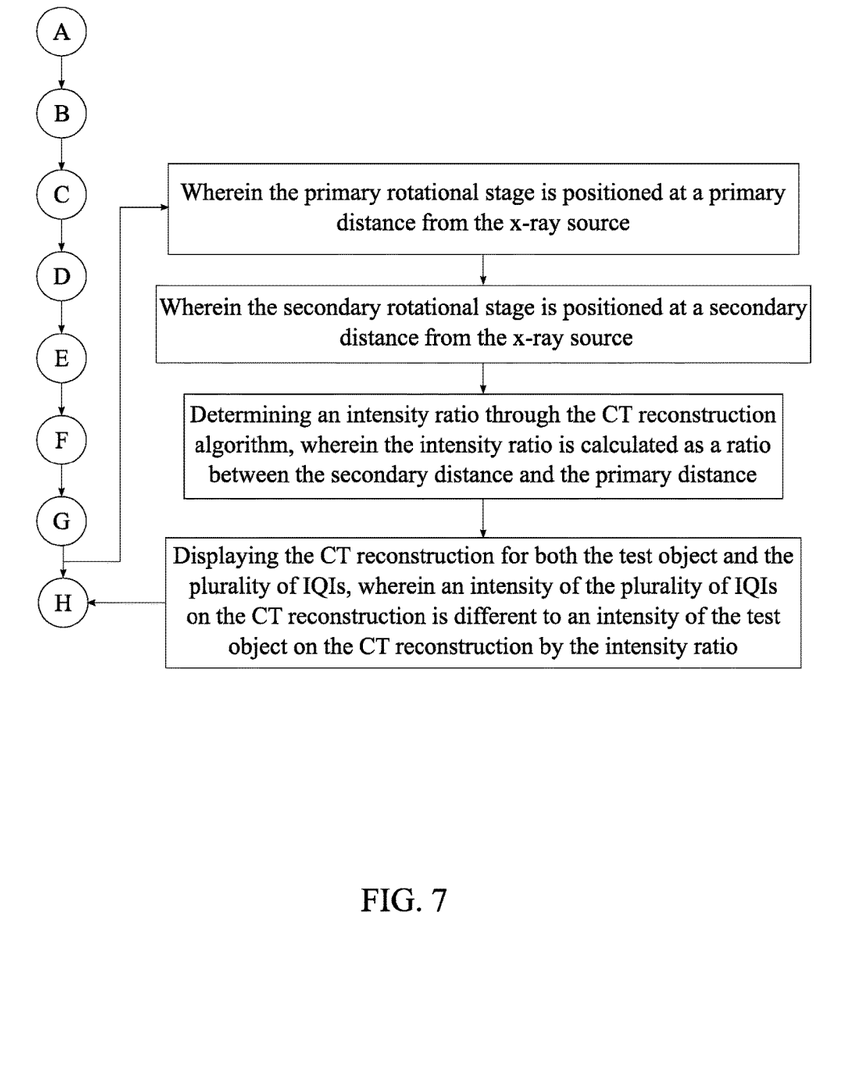
FIG. 7 is a flowchart illustrating the basic overall process of calculating the intensity ratio.

Since the primary rotational stage and the secondary rotational stage are positioned at different distances from the x-ray source and a magnitude factor is used to scale the plurality of IQIs for the CT reconstruction, an intensity of the plurality of IQIs will also be scaled within the CT reconstruction. More specifically, an intensity of the CT reconstruction for the plurality of IQIs needs to be relatable to the radiation attenuation values of the test object, wherein the radiation attenuation value is a result of a radiation spectrum of the x-ray source and the material composition of the test object. As shown in FIG. 7, the present invention determines an intensity ratio by calculating a ratio between the secondary distance and the primary distance. Referring to the previous example of using a 0.4-inch diameter rod on the secondary rotational stage, wherein the secondary distance is 24-inches and the primary distance is 30-inches, an intensity of the 0.4-inch diameter rod would be reduced to 80% of the expected value. More specifically, when the CT reconstruction for both the plurality of IQIs and the test object is displayed, an intensity of the plurality of IQIs is different to an intensity of the test object by the intensity ratio if the material of the plurality of IQIs is the same material as the test object.

The x-ray beam emitted from the x-ray source can vary in different embodiments of the present invention. As an example, in one embodiment of the present invention, a polychromatic beam can be used. In another embodiment of the present invention, a monochromatic beam can be used. Regardless of the x-ray beam characteristics, the overall arrangement of the x-ray source, the primary rotational stage, the secondary rotational stage, and the x-ray beam detector remains unchanged.

Although the invention has been explained in relation to its preferred embodiment, it is to be understood that many other possible modifications and variations can be made without departing from the spirit and scope of the invention as hereinafter claimed.

What is claimed is:

1. A method of representing internal conditions in computed tomography (CT) comprising the steps of:
    (A) providing at least one remote server, wherein the at least one remote server comprises a computed tomography (CT) reconstruction algorithm, wherein the at least one remote server manages a synching mechanism;
    (B) providing an x-ray source, a primary rotational stage, a secondary rotational stage, and an x-ray beam detector, wherein the x-ray source, the primary rotational stage, the secondary rotational stage, and the x-ray beam detector are linearly aligned to each other, wherein the primary rotational stage and the secondary rotational stage are operatively engaged with the synching mechanism;
    (C) providing a test object, wherein the test object is situated on the primary rotational stage;
    (D) providing a plurality of image quality indicators (IQI), wherein the plurality of IQIs is situated on the secondary rotational stage, wherein a position of each of the plurality of IQIs corresponds to a selected coordinate of the test object;
    (E) rotationally synchronizing the primary rotational stage with the secondary rotational stage through the syncing mechanism managed by the at least one remote server;
    (F) projecting an x-ray beam from the x-ray source towards the plurality of IQIs and the test object;
    (G) detecting and accumulating a plurality of projection data at the x-ray beam detector, wherein the plurality of projection data is generated when the x-ray beam intersects the plurality of IQIs and the test object; and
    (H) developing a CT reconstruction for both the test object and the plurality of IQIs through the CT reconstruction algorithm, wherein the CT reconstruction is developed by utilizing the plurality of projection data.

2. The method of representing the internal conditions in CT as claimed in claim 1, wherein a size ratio between the CT reconstruction for the test object and the CT reconstruction for the plurality of IQIs is 1:1.

3. The method of representing the internal conditions in CT as claimed in claim 1, wherein the secondary rotational stage is positioned in between the x-ray source and the primary rotational stage.

4. The method of representing the internal conditions in CT as claimed in claim 1, wherein the secondary rotational stage is positioned in between the primary rotational stage and the x-ray beam detector.

5. The method of representing the internal conditions in CT as claimed in claim 1 further comprises the steps of:
    developing a plurality of projection images at the x-ray beam detector, wherein the plurality of projection images is developed from the plurality of projection data and saved on the at least one remote server, wherein each of the plurality of projection images comprises an angular orientation and a radial distance;
    generating a plurality of cross-sectional slices from the plurality of projection images through the CT reconstruction algorithm, wherein the plurality of cross-sectional slices is based upon the angular orientation and the radial distance of each of the plurality of projection images; and
    organizing the plurality of cross-sectional slices through the CT reconstruction algorithm to develop the CT reconstruction for both the test object and the plurality of IQIs.

6. The method of representing the internal conditions in CT as claimed in claim 1 further comprises the steps of:
    wherein the primary rotational stage is positioned at a primary distance from the x-ray source;
    wherein the secondary rotational stage is positioned at a secondary distance from the x-ray source;
    deriving a magnitude factor for the CT reconstruction for the plurality of IQIs through the CT reconstruction algorithm as a ratio between the secondary distance and the primary distance; and
    scaling the plurality of projection data from the plurality of IQIs to match the plurality of projection data from the test object, wherein the plurality of projection data from the plurality of IQIs is scaled by an inverse of the magnitude factor through the CT reconstruction algorithm.

7. The method of representing the internal conditions in CT as claimed in claim 6 further comprises the steps of:
    determining an intensity ratio for the plurality of IQIs through the CT reconstruction algorithm, wherein the intensity ratio is calculated as a ratio between the secondary distance and the primary distance; and
    displaying the CT reconstruction for both the test object and the plurality of IQIs, wherein an intensity of the plurality of IQIs on the CT reconstruction is different to an intensity of the test object on the CT reconstruction by the intensity ratio.

8. The method of representing the internal conditions in CT as claimed in claim 1, wherein the x-ray beam is a polychromatic beam.

9. The method of representing the internal conditions in CT as claimed in claim 1, wherein the x-ray beam is a monochromatic beam.

10. The method of representing the internal conditions in CT as claimed in claim 1, wherein the plurality of IQIs is a plurality of internal IQIs.

11. The method of representing the internal conditions in CT as claimed in claim 1, wherein the plurality of IQIs is a plurality of external IQIs.

12. The method of representing the internal conditions in CT as claimed in claim 1, wherein the primary rotational stage is rotationally synchronized with the secondary rotational stage mechanically.

* * * * *